United States Patent
Doyle et al.

(10) Patent No.: US 6,740,099 B1
(45) Date of Patent: May 25, 2004

(54) SURGICAL TOOL FOR TRIMMING WIRE STRANDS

(76) Inventors: Mark Doyle, 4804 50th St., San Diego, CA (US) 92115; John T. Rice, 31 Red Rail Farm La., Lincoln, MA (US) 01773; Douglas A. Fogg, 15 S. Pleasant St., Merrimac, MA (US) 01860

( * ) Notice: Subject to any disclaimer, the term of this patent is extended or adjusted under 35 U.S.C. 154(b) by 324 days.

(21) Appl. No.: 10/046,344

(22) Filed: Oct. 19, 2001

Related U.S. Application Data (60) Provisional application No. 60/242,235, filed on Oct. 20, 2000.

(51) Int. Cl.$^7$ ............................................. A61B 17/04
(52) U.S. Cl. ...................................................... 606/148
(58) Field of Search ........................................ 606/148

(56) References Cited

U.S. PATENT DOCUMENTS

| | | | | |
|---|---|---|---|---|
| 3,354,478 A | * | 11/1967 | Allen | 7/107 |
| 3,871,379 A | * | 3/1975 | Clarke | 606/148 |
| 4,369,787 A | * | 1/1983 | Lasner et al. | 606/138 |
| 4,662,068 A | * | 5/1987 | Polonsky | 30/124 |
| 5,452,513 A | * | 9/1995 | Zinnbauer et al. | 30/140 |
| 5,499,990 A | * | 3/1996 | Schulken et al. | 606/144 |
| 5,565,122 A | * | 10/1996 | Zinnbauer et al. | 219/227 |
| 6,183,485 B1 | * | 2/2001 | Thomason et al. | 606/148 |
| 6,331,182 B1 | * | 12/2001 | Tiefenbrun et al. | 606/144 |
| 6,332,889 B1 | * | 12/2001 | Sancoff et al. | 606/148 |

* cited by examiner

Primary Examiner—Gary Jackson
(74) Attorney, Agent, or Firm—Pandiscio & Pandiscio (57) ABSTRACT

Apparatus is disclosed for manipulating a material during a surgical procedure, the apparatus comprising
a first jaw having a distal end and a proximal end and
a second jaw having a distal end and a proximal end, the proximal end of the first jaw and the proximal end of the second jaw being pivotally connected to one another so as to open and close the distal end of the first jaw and the distal end of said second jaw relative to one another; a gripping mechanism being formed by the first jaw and the second jaw; a cutting mechanism being formed by said first jaw and the second jaw; and a storage mechanism being formed by the first jaw and the second jaw.

24 Claims, 8 Drawing Sheets

SURGICAL TOOL FOR TRIMMING WIRE STRANDS

REFERENCE TO PRIOR PATENT APPLICATION

This patent application claims benefit of prior U.S. Provisional Patent Application Serial No. 60/242,235, filed Oct. 20, 2000 now abandoned by Mark Doyle et al. for SURGICAL TOOL FOR TRIMMING WIRE STRANDS, which prior patent application is hereby incorporated herein by reference.

FIELD OF THE INVENTION

This invention relates to surgical apparatus in general, and more particularly to devices for trimming wire strands during a surgical procedure.

BACKGROUND OF THE INVENTION

In copending U.S. patent application Ser. No. 09/368,273, filed Aug. 31, 1999 by Gregory E. Sancoff et al. for SURGICAL SUTURING INSTRUMENT AND METHOD OF USE, which patent application is hereby incorporated herein by reference, there is disclosed a suturing instrument for passing strands of wire suture through tissue and then twisting the ends of the wire strands together, whereby to suture the tissue.

As a consequence of this procedure, at the conclusion of the suturing operation, the twisted ends of the wire suture typically stand proud above the tissue. For many applications, this does not present a problem. However, in other applications, the fact that the twisted wire ends project above the tissue can present a problem. As a result, it may be desirable to perform a subsequent, secondary operation on the twisted wire ends so as to reduce the profile of the wire suture. For example, it may be desirable to bend the twisted wire ends down toward the tissue, and/or to trim away a portion of those ends, etc.

SUMMARY OF THE INVENTION

As a result, one object of the present invention is to provide a surgical tool for reducing the profile of twisted wire ends projecting above tissue.

Another object of the present invention is to provide a surgical tool for bending the twisted wire ends down toward the tissue.

And another object of the present invention is to provide a surgical tool for trimming off a portion of the twisted wire ends projecting above tissue.

Still another object of the present invention is to provide a surgical tool for trimming off a portion of the twisted wire ends projecting above tissue, and for releasably capturing those trimmed-off wire ends to the tool.

And another object of the present invention is to provide a surgical tool which can be used to perform operations on filament strands positioned within the body, wherein those filament strands may be formed out of metal wire and non-metal filaments including, but not limited to, monofilament suture, etc.

These and other objects are addressed by the present invention, which comprises a novel surgical tool for trimming wire strands during a surgical procedure.

In one form of the invention, there is provided apparatus for manipulating a material during a surgical procedure, the apparatus comprising: a first jaw having a distal end and a proximal end; a second jaw having a distal end and a proximal end, the proximal end of the first jaw and the proximal end of the second jaw being pivotally connected to one another so as to open and close the distal end of the first jaw and the distal end of the second jaw relative to one another; a gripping mechanism for capturing the material, the gripping mechanism being formed by the first jaw and the second jaw; a cutting mechanism for shearing the material, the cutting mechanism being formed by the first jaw and the second jaw; and a storage mechanism for trapping the material, the storage mechanism being formed by the first jaw and the second jaw.

In another form of the invention, there is provided a method for manipulating a material during a surgical procedure, the method comprising: providing apparatus for manipulating a material during a surgical procedure, the apparatus comprising: a first jaw having a distal end and a proximal end; a second jaw having a distal end and a proximal end, the proximal end of the first jaw and the proximal end of the second jaw being pivotally connected to one another so as to open and close the distal end of the first jaw and the distal end of the second jaw relative to one another; a gripping mechanism for capturing the material, the gripping mechanism being formed by the first jaw and the second jaw; a cutting mechanism for shearing the material, the cutting mechanism being formed by the first jaw and the second jaw; and a storage mechanism for trapping the material, the storage mechanism being formed by the first jaw and the second jaw; positioning the first jaw and the second jaw adjacent to the material; capturing the material with the gripping mechanism; positioning the material captured with the gripping mechanism; and releasing the first jaw and the second jaw from the material.

And in still another form of the invention, there is provided a method for manipulating a material during a surgical procedure, the method comprising: providing apparatus for manipulating a material during a surgical procedure, the apparatus comprising: a first jaw having a distal end and a proximal end; a second jaw having a distal end and a proximal end, the proximal end of the first jaw and the proximal end of the second jaw being pivotally connected to one another so as to open and close the distal end of the first jaw and the distal end of the second jaw relative to one another; a gripping mechanism for capturing the material, the gripping mechanism being formed by the first jaw and the second jaw; a cutting mechanism for shearing the material, the cutting mechanism being formed by the first jaw and the second jaw; and a storage mechanism for trapping the material, the storage mechanism being formed by the first jaw and the second jaw; and shearing the material with the cutting mechanism, wherein the material projecting away from tissue is sheared therefrom.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

Looking first at FIGS. 1–4, there is shown a surgical tool 5 formed in accordance with the present invention. Surgical tool 5 generally comprises a shaft 100 having a distal end 105 and a proximal end 110, a pair of jaws 200 disposed at the distal end of shaft 100, and a handle 300 disposed at the proximal end of shaft 100.

Shaft 100 and handle 300 may be any of the many shafts and handles known in the art, whereby when handle 300 is appropriately activated at the proximal end of the shaft, jaws 200 may be correspondingly opened and closed relative to one another. Surgical tool 5 is shown in a configuration with jaws 200 opened relative to one another (see FIGS. 1 and 2) and is also shown in another configuration with jaws 200 closed relative to one another (see FIGS. 3 and 4). By way of example but not limitation, shaft 100 and handle 300 may be of the type described and illustrated in U.S. Pat. Nos. 5,152,780 and 5,219,357, which patents are hereby incorporated herein by reference.

Figure 1:
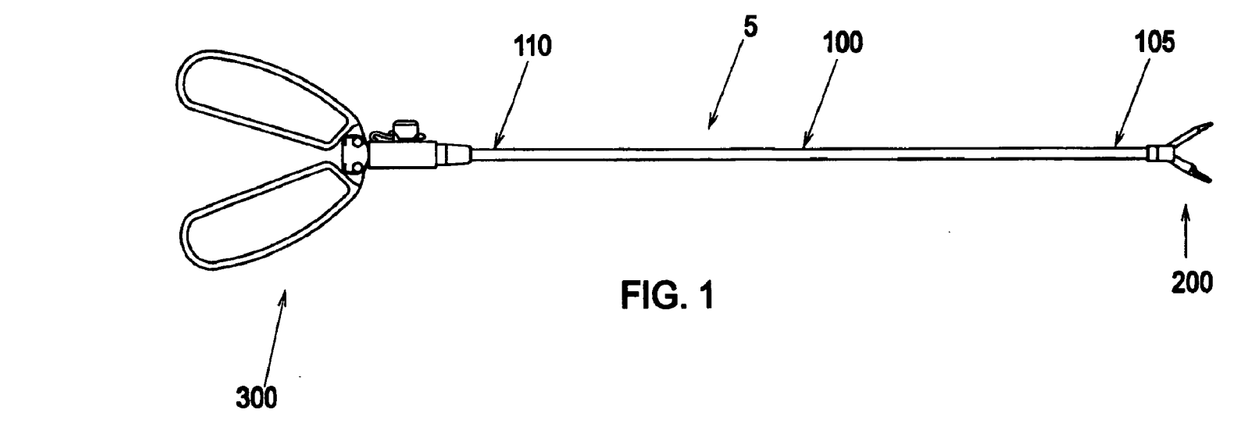
FIG. 1 is a side view of a surgical tool formed in accordance with the present invention, wherein the surgical tool is shown with its jaws open.
Figure 2:
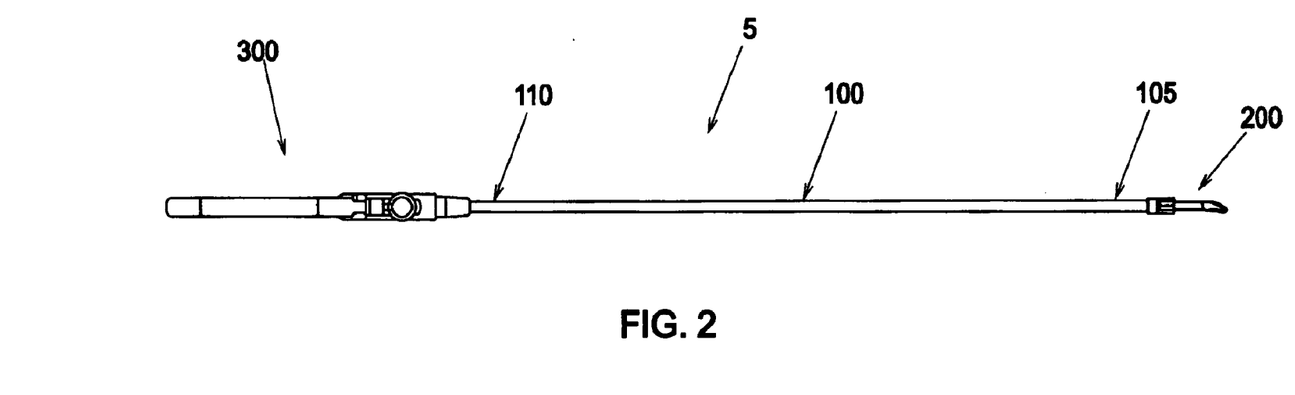
FIG. 2 is a top view of the surgical tool shown in FIG. 1.
Figure 3:
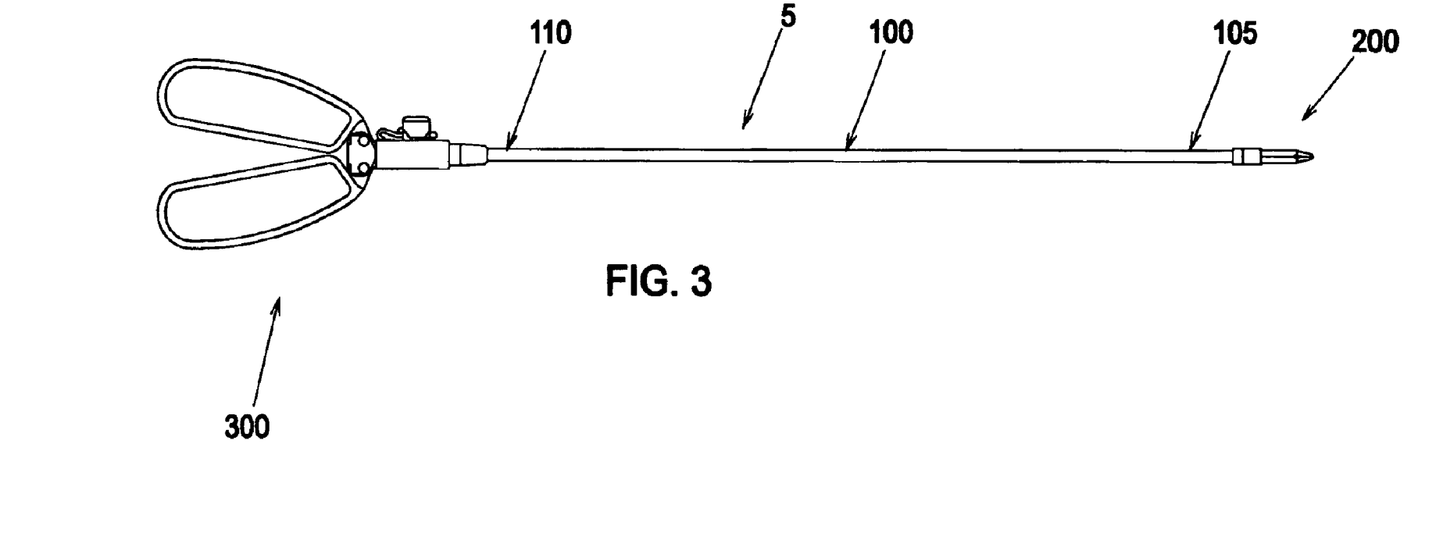
FIG. 3 is a side view of the surgical tool shown in FIG. 1, except that the surgical tool is shown with its jaws closed.
Figure 4:
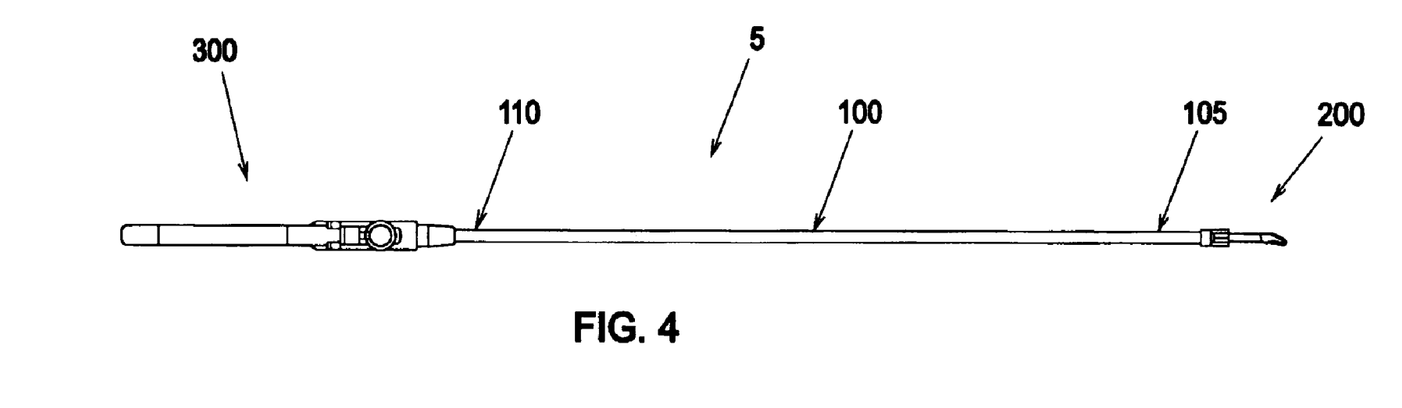
FIG. 4 is a top view of the surgical tool shown in FIG. 3.
Figure 5:
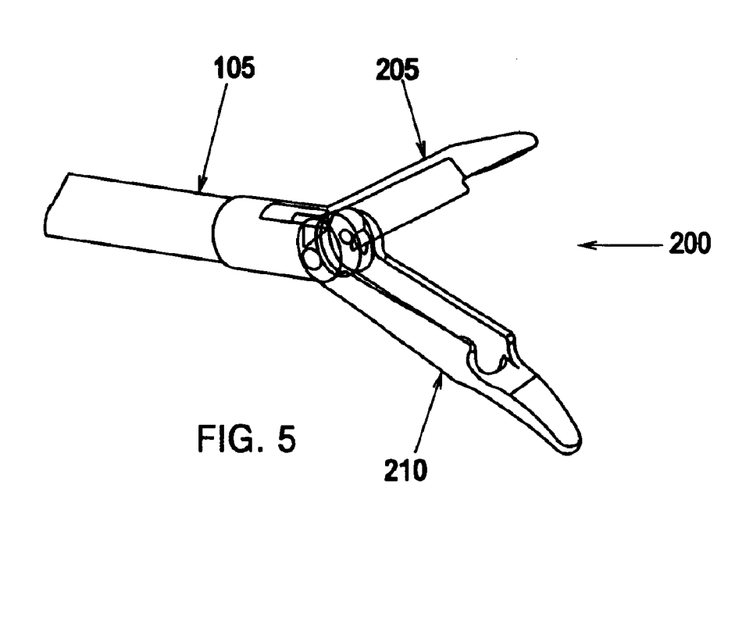
FIGS. 5 and 6 are perspective views of the distal end of the surgical tool shown in FIGS. 1 and 2.
Figure 6:
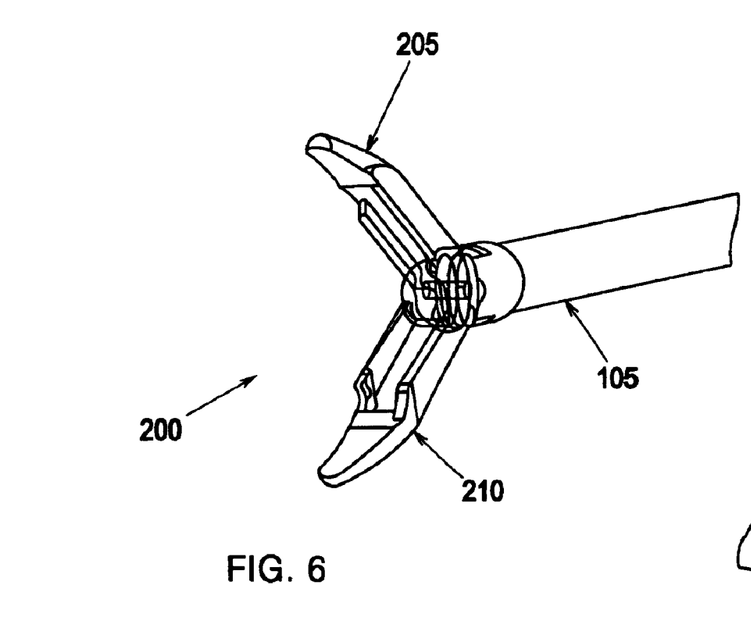
Figure 7:
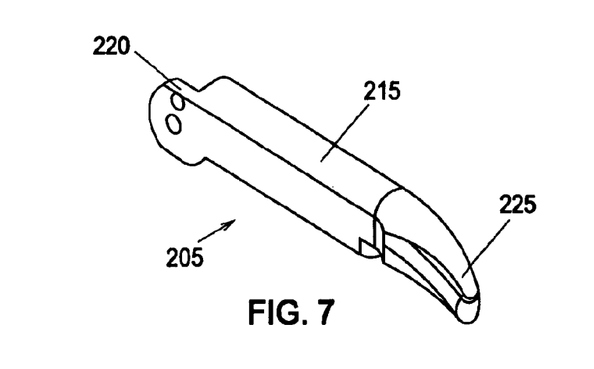
FIGS. 7–11 are views showing additional construction features of the first, or "top", jaw.
Figure 8:
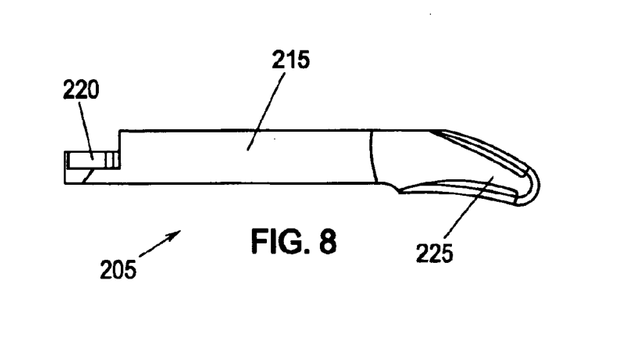
Figure 9:
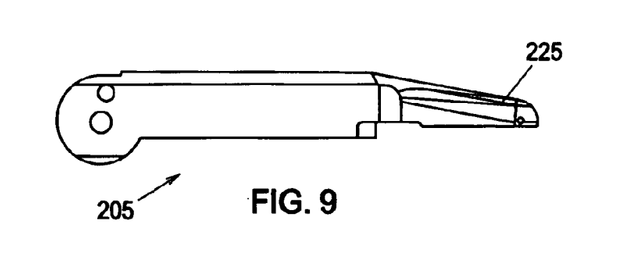

Looking next at FIGS. 5 and 6, in a preferred embodiment of the present invention, jaws 200 comprise a first jaw 205 and a second jaw 210. As described herein, first jaw 205 is sometimes hereinafter referred to as a "top" jaw and second jaw 210 is sometimes hereinafter referred to as a "bottom" jaw.

Figure 10:
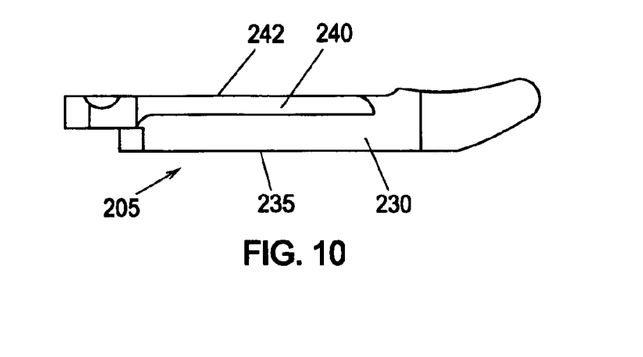
Figure 11:
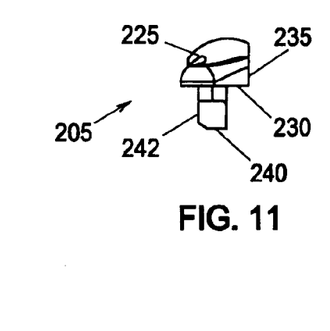
Figure 12:
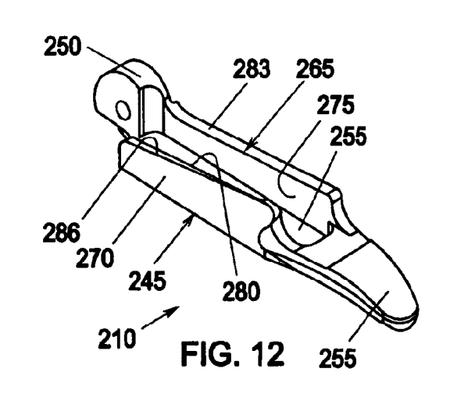
FIGS. 12–16 are views showing additional construction features of the second, or "bottom", jaw.
Figure 13:
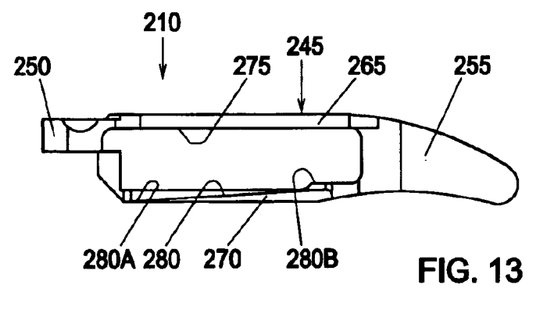
Figure 14:
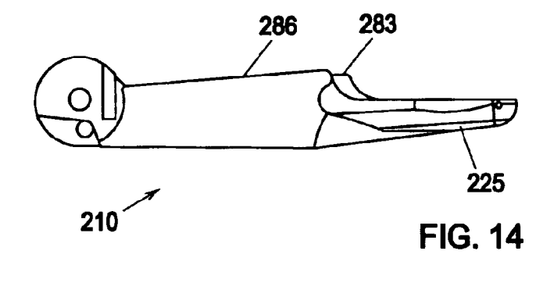
Figure 15:
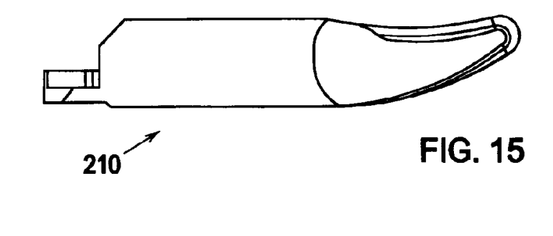
Figure 16:
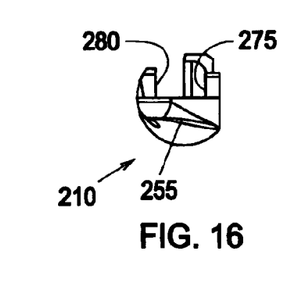

Looking next at FIGS. 8–11, in a preferred embodiment of the invention, top jaw 205 comprises a body 215 having, at its proximal end, a mounting flange 220 for pivotally connecting top jaw 205 to shaft 100 (see FIGS. 5 and 6). The top jaw's body 215 terminates, at its distal end, in a nose portion 225. In order to improve visibility and wire manipulation, nose portion 225 preferably, but not necessarily, (i) curves to one side of the longitudinal axis of body 215 (see FIGS. 7, 8, 10 and 11), and (ii) tapers downward toward the distal tip (see FIGS. 9 and 11). The top jaw's body portion 215 includes a flat bottom surface 230 (FIGS. 10 and 11), a shearing surface 235 extending at a right angle to bottom surface 230, and a foot 240 extending downward, away from bottom surface 230. Foot 240 comprises an outside wall surface 242 (FIGS. 10 and 11).

In another preferred embodiment of the present invention, nose portion 225 may be configured to taper downward toward the distal tip without curving away from the longitudinal axis of body 215. This straight tapered tip (not shown) provides an alternative to the curved tip profile (see FIGS. 7, 8, 10 and 11) while still affording visibility and wire manipulation.

Looking next at FIGS. 12–16, in a preferred embodiment of the present invention, bottom jaw 210 comprises a body 245 having, at its proximal end, a mounting flange 250 for pivotally connecting bottom jaw 210 to shaft 100. The bottom jaw's body 245 terminates, at its distal end, in a nose portion 255. In order to improve visibility and wire manipulation, nose portion 255 preferably, but not necessarily, (i) curves to one side of body 245 (see FIGS. 12, 13, 15 and 16), and (ii) tapers upward toward the distal tip (see FIGS. 14 and 16). The bottom jaw's body 245 includes a flat bottom surface 260 and a pair of raised side walls 265, 270. Raised side wall 265 includes a shearing surface 275 (see FIGS. 12, 13 and 16) which cooperates with the shearing surface 235 of top jaw 205 (FIG. 11) to cut suture wire, as will hereinafter be discussed. Raised side wall 270 includes a side wall surface 280 (see FIGS. 12, 13 and 16) which is relieved outwardly as it extends proximally from an innermost section 280B (FIG. 13) to an outermost section 280A. Side wall surface 280 is disposed so that its innermost section 280B will cooperate with outside wall surface 242 (FIG. 11) of foot 240 of top jaw 205 so as to keep shearing surfaces 235 (FIG. 11) and 275 (FIG. 16) in engagement with one another as the two jaws close, as will hereinafter be discussed in further detail. At the same time, however, side wall surface 280 is disposed so that its outermost section 280A (FIG. 13) will be spaced from outside wall surface 242 (FIG. 11) of foot 240 of top jaw 205 when jaws 200 are closed, so as to keep surfaces 280A and 242 from becoming shearing surfaces. In addition to the foregoing, the top surfaces 283 (FIGS. 12 and 14) and 286 of side walls 265 and 270, respectively, taper downward in the distal direction so as to minimize the tendency of the twisted wire ends to escape distally as jaws 200 are closed.

Surgical tool 5 may be used to bend twisted wire ends down toward tissue, so as to reduce their profile, and/or to trim off a portion of the twisted wire ends, whereby to reduce the profile of the suture remaining in the tissue.

More particularly, if surgical tool 5 is to be used to bend twisted wire ends down to tissue, the tool may be used as follows. First, the tool typically has its jaws 200 closed to the position shown in FIGS. 3 and 4, whereby the jaws may be easily and safely passed to the surgical site, which may be a so-called closed surgical site such as a laparoscopic or arthroscopic site. Next, jaws 200 are positioned close to the twisted wire ends, and the jaws are opened. Then the two jaws 205, 210 are positioned on either side of the twisted wire ends and the jaws 205, 210 are closed so that the twisted wire ends are securely captured between the two nose portions 225 (FIG. 7), 255(FIG. 12) of the jaws 205, 210. However, no shearing of the twisted wire ends will take place, since nose portions 225, 255 are substantially flat and devoid of shearing surfaces. These nose portions 225, 255 may be textured so as to enhance secure gripping of the twisted wire ends without damaging the same. Then, while the twisted wire ends remain captured between the two jaws 205, 210, the handle 300 is manipulated so as to bend the twisted wire ends down against the tissue, whereby to lower their profile relative to the issue.

Alternatively, if surgical tool 5 is to be used to trim off a portion of the twisted wire ends, the tool may be used as follows. First, the tool typically has its jaws 200 closed to the position shown in FIGS. 3 and 4, whereby the tool 5 may be easily and safely passed to the surgical site, which may be a so-called closed surgical site such as a laparoscopic or arthroscopic site. Next, the jaws 200 are positioned close to the twisted wire ends, and the two jaws 205, 210 are opened. Then the jaws 205, 210 are positioned over the twisted wire ends with the shearing surfaces 235 and 275 facing the tissue (FIG. 17) and the jaws closed (FIG. 18) so that the twisted wire ends are severed from the remainder of the suture wire at the surgical site and, simultaneously, the severed wire ends are releasably captured to the tool.

Figure 17:
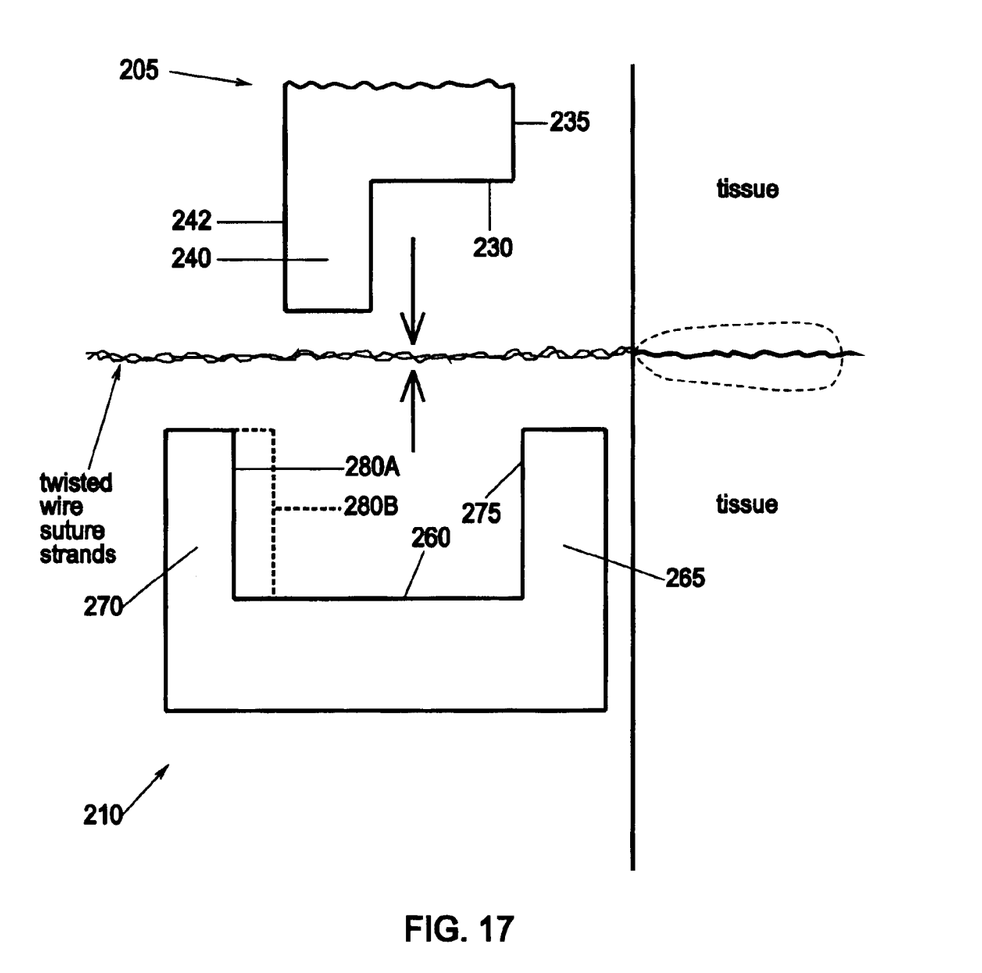
FIG. 17 is a schematic side view showing the surgical tool with its jaws open and just prior to engaging twisted wire ends projecting out of tissue.
Figure 18:
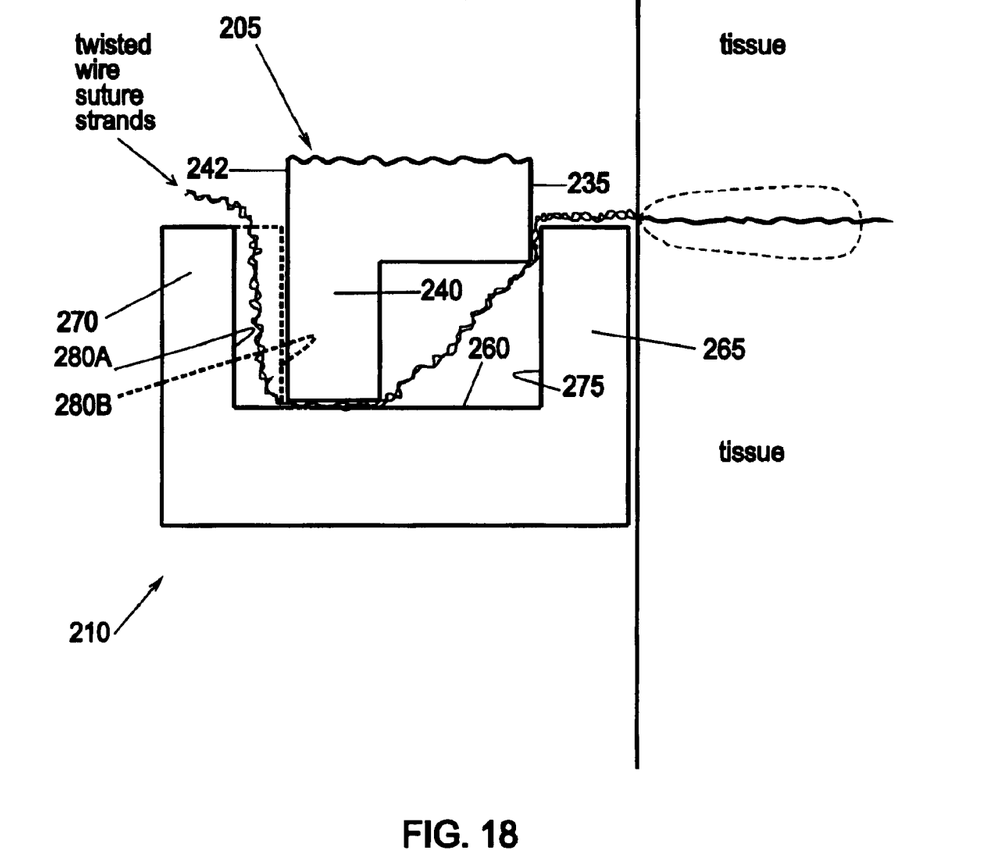
FIG. 18 is a schematic side view showing the surgical tool with its jaws closed and just after cutting off twisted wire ends projecting out of tissue, with the closed jaws capturing the cut-off twisted wire ends to the tool.
Figure 19:
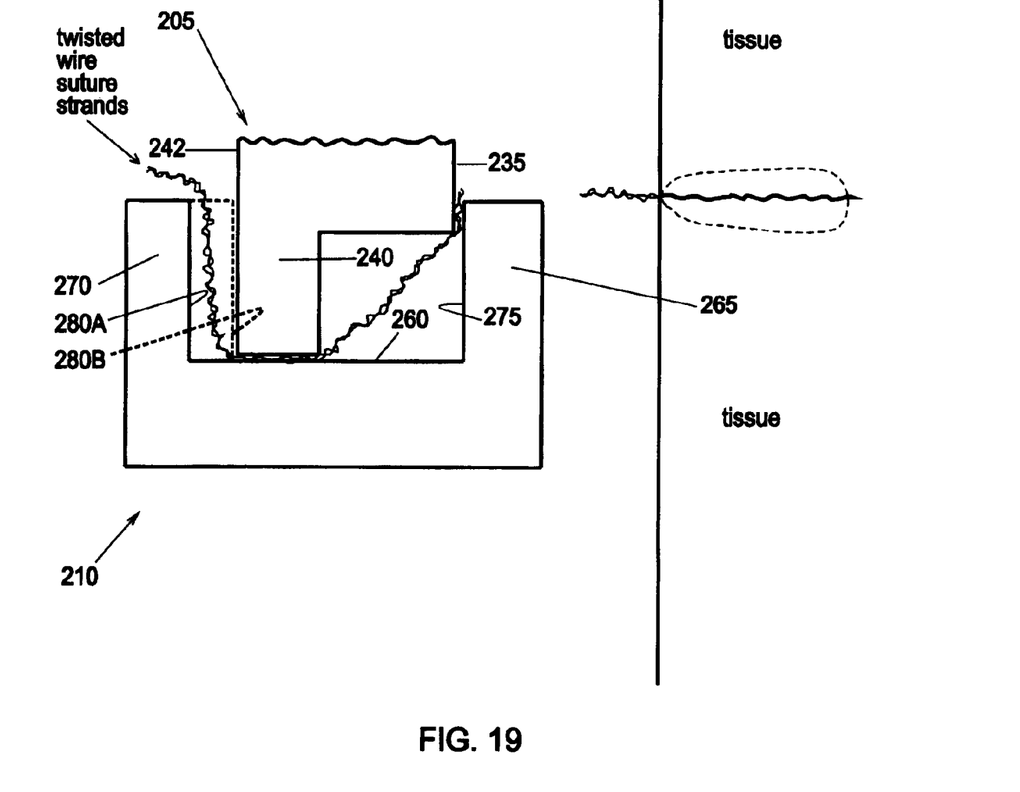
FIG. 19 is a schematic side view showing the surgical tool with its jaws closed and just after it has been lifted away from the tissue, with the closed jaws carrying the cut-off twisted wire ends away from the tissue.

More particularly, and looking now at FIGS. 17 and 18, as the top and bottom jaws 205, 210 begin to close, the top jaw's foot 240 engages the twisted wire ends and bends them down into the bottom jaw's trap, i.e., the region bounded by the bottom jaw's flat bottom surface 260 and its raised side walls 265, 270. As the jaws close further, the top jaw's shear surface 235 passes by the bottom jaw's shear surface 275, thereby severing the twisted wire suture strands near the surface of the tissue. At the same time, the top jaw's foot 240 will pin the severed twisted wire strands to the bottom surface 260 of bottom jaw 210, whereby to keep the severed strands bound to the tool and prevent them from migrating into the surrounding anatomy as the tool is withdrawn from the tissue (see FIG. 19). In this respect it will also be appreciated that side wall surface 280A (FIGS. 13, 17 and 18) is deliberately positioned sufficiently far outboard of outside wall surface 242 of foot 240 that surfaces 280A and 242 will not shear twisted wire strands during jaw closing.

It should also be appreciated that the aforementioned tool may also be used to trim non-metal sutures, e.g., it may be used to trim monofilament or braided sutures at a surgical site, or to trim other inanimate objects, or to trim tissue, etc.

In addition to the foregoing, the aforementioned tool may be used to grasp tissue, or the tool may be used for blunt tissue dissection, etc.

What is claimed is:

1. Apparatus for manipulating a material during a surgical procedure, said apparatus comprising:
   a first jaw having a distal end and a proximal end;
   a second jaw having a distal end and a proximal end, said proximal end of said first jaw and said proximal end of said second jaw being pivotally connected to one another so as to open and close said distal end of said first jaw and said distal end of said second jaw relative to one another;
   a gripping mechanism for capturing the material, said gripping mechanism being formed by said first jaw and said second jaw;
   a cutting mechanism for shearing the material, said cutting mechanism being formed by said first jaw and said second jaw; and
   a storage mechanism for trapping the material, said storage mechanism being formed by said first jaw and said second jaw.

2. Apparatus according to claim 1 wherein said gripping mechanism comprises a first gripping surface on said first jaw and a second gripping surface on said second jaw, with said first gripping surface and said second gripping surface being disposed in opposition to one another, wherein the material is positioned between the first gripping surface and the second gripping surface with said first jaw and said second jaw apart from one another, and then said first jaw and said second jaw are closed toward one another to cause said first gripping surface and said second gripping surface to move toward one another so as to capture the material therebetween.

3. Apparatus according to claim 2 wherein each of said first gripping surface and said second gripping surface is substantially flat.

4. Apparatus according to claim 2 wherein each of said first gripping surface and said second gripping surface is textured so as to enhance secure capture of the material.

5. Apparatus according to claim 2 wherein each of said first gripping surface and said second gripping surface are devoid of a shearing surface so as to leave intact the material after capture.

6. Apparatus according to claim 2 wherein each of said first gripping surface and said second gripping surface are adjacent to said distal end of said first jaw and said distal end of said second jaw, respectively.

7. Apparatus according to claim 1 wherein said cutting mechanism comprises a first shearing surface on said first jaw and a second shearing surface on said second jaw, with said first shearing surface and said second shearing surface being disposed in opposition to one another, wherein the material is positioned between said first shearing surface and said second shearing surface with said first jaw and said second jaw apart from one another, and then said first jaw and second jaw are closed toward one another to cause said first shearing surface and said second shearing surface to pass by one another so as to sever the material therebetween.

8. Apparatus according to claim 7 further comprising a first raised sidewall on said first jaw and a second raised sidewall on said second jaw, said first raised sidewall and said second raised sidewall comprising said first shearing surface and said second shearing surface, respectively.

9. Apparatus according to claim 1 wherein said storage mechanism comprises a first storage surface on said first jaw and a second storage surface on said second jaw, with said first storage surface and said second storage surface being disposed in opposition to one another, whereby the material is positioned between said first storage surface and said second storage surface with said first jaw and said second jaw apart from one another, and then said first jaw and said second jaw are closed toward one another to cause said first storage surface and said second storage surface to move toward one another so as to pin said material therebetween.

10. Apparatus according to claim 9 wherein said storage mechanism has a first side and a second side, said cutting mechanism being configured on said first side of said storage mechanism, said first storage surface and said second storage surface forming a passageway therebetween on said second side of said storage mechanism, whereby closing said first jaw and said second jaw toward one another causes said cutting mechanism to shear said material at said first side of said storage mechanism while simultaneously pinning the material between said first storage surface and said second storage surface and keeping the material intact at said second side of said storage mechanism.

11. Apparatus according to claim 1 wherein said cutting mechanism is disposed on said proximal end of each of said first jaw and said second jaw, respectively.

12. Apparatus according to claim 1 wherein said storage mechanism is formed on said proximal end of each of said first jaw and said second jaw, respectively.

13. Apparatus according to claim 1 wherein each of said first jaw and said second jaw define a longitudinal axis from said distal end to said proximal end, wherein a first side and a second side are formed in opposition to said longitudinal axis on each of said first jaw and said second jaw, respectively, wherein said cutting mechanism is disposed on said first side of each of said first jaw and said second jaw, respectively, and said storage mechanism is disposed on said second side of each of said first jaw and said second jaw, respectively.

14. Apparatus according to claim 13 wherein said cutting mechanism and storage mechanism are substantially aligned along an axis perpendicular to said longitudinal axis.

15. Apparatus according to claim 13 wherein at least a portion of a surface of said first jaw is in opposition to another surface of said second jaw, and further wherein said surface of said first jaw tapers away from said surface of said second jaw along said longitudinal axis toward said proximal end of said first jaw.

16. Apparatus according to claim 13 wherein said first jaw is configured to form an innermost section adjacent to said proximal end thereof, and further wherein said first jaw is configured to form an outermost section adjacent to said proximal end thereof, whereby said innermost section allows the material to pass therethrough intact and said outermost section acts to engage a corresponding portion of said second jaw so as to position said cutting mechanism as said first jaw and said second jaw close toward one another.

17. Apparatus according to claim 13 wherein said gripping mechanism is disposed at said distal end of each of said first jaw and said second jaw, and said distal end of each of said first jaw and said second jaw are curved with respect to said longitudinal axis in a plane perpendicular to an axis of rotation between said first jaw and said second jaw.

18. Apparatus according to claim 1 further comprising a shaft having a proximal end and a distal end, said first and second jaws being positionably disposed at said distal end of said shaft, and a handle being disposed at said proximal end of said shaft, wherein activation of said handle selectively opens and closes said first jaw and said second jaw with respect to one another.

19. Apparatus according to claim 1 wherein the material is a filament.

20. Apparatus according to claim 1 wherein the material is tissue.

21. A method for manipulating a material during a surgical procedure, said method comprising:

providing apparatus for manipulating a material during a surgical procedure, said apparatus comprising:
 a first jaw having a distal end and a proximal end;
 a second jaw having a distal end and a proximal end, said proximal end of said first jaw and said proximal end of said second jaw being pivotally connected to one another so as to open and close said distal end of said first jaw and said distal end of said second jaw relative to one another;
 a gripping mechanism for capturing the material, said gripping mechanism being formed by said first jaw and said second jaw;
 a cutting mechanism for shearing the material, said cutting mechanism being formed by said first jaw and said second jaw; and
 a storage mechanism for trapping the material, said storage mechanism being formed by said first jaw and said second jaw;

positioning said first jaw and said second jaw adjacent to the material;

capturing the material with said gripping mechanism;

positioning the material captured with said gripping mechanism; and releasing said first jaw and said second jaw from the material.

22. A method according to claim 21 wherein the material is a twisted wire closure projecting from tissue, and further wherein the twisted wire closure is bent with said gripping mechanism so as to reduce the profile projecting from the tissue.

23. A method for manipulating a material during a surgical procedure, said method comprising:

providing apparatus for manipulating a material during a surgical procedure, said apparatus comprising:
 a first jaw having a distal end and a proximal end;
 a second jaw having a distal end and a proximal end, said proximal end of said first jaw and said proximal end of said second jaw being pivotally connected to one another so as to open and close said distal end of said first jaw and said distal end of said second jaw relative to one another;
 a gripping mechanism for capturing the material, said gripping mechanism being formed by said first jaw and said second jaw;
 a cutting mechanism for shearing the material, said cutting mechanism being formed by said first jaw and said second jaw; and
 a storage mechanism for trapping the material, said storage mechanism being formed by said first jaw and said second jaw; and shearing the material with said cutting mechanism, wherein the material projecting away from tissue is sheared therefrom.

24. A method according to claim 23 further comprising the step of releasably capturing the material sheared away from the tissue.

* * * * *